United States Patent [19]

Simon et al.

[11] Patent Number: 5,032,363
[45] Date of Patent: Jul. 16, 1991

[54] ION SELECTIVE PART OF AN APPARATUS FOR THE DETERMINATION OF THE CONCENTRATION OF IONS AND PROCESS FOR THE PREPARATION OF POLYMERIC MATERIALS CONTAINING HYDROPHILIC GROUPS

[75] Inventors: Wilhelm Simon, Zurich, Switzerland; Lucas F. J. Dürselen, Klettgau-Erzingen, Fed. Rep. of Germany

[73] Assignee: Willi Moller AG, Zurich, Switzerland

[21] Appl. No.: 235,843

[22] Filed: Aug. 24, 1988

[30] Foreign Application Priority Data

Sep. 4, 1987 [CH] Switzerland .................. 3403/87

[51] Int. Cl.$^5$ .................................. C08K 5/09
[52] U.S. Cl. .................. 422/82.03; 524/17; 524/184; 524/220; 524/503; 524/569; 204/416; 204/419
[58] Field of Search ............ 524/503, 569, 220, 17; 422/82.03; 204/416, 419

[56] References Cited

U.S. PATENT DOCUMENTS 4,608,149  8/1986  Daniel et al. .................. 204/418
4,783,496  11/1988  Simon et al. .................. 526/284

FOREIGN PATENT DOCUMENTS 185267  of 0000  European Pat. Off.
0219742  4/1987  European Pat. Off.
5974144  of 0000  Japan.

OTHER PUBLICATIONS

Satchwill P. Harrison, "Synthesis and Characterization of New Polyvinylchloride Membranes for Enhanced Adhesion on Electrode Surfaces," J. Electroanal. Chem., 202(1986), 75–81.
Oesch, et al., "Ion-Selective Membrane Electrodes for Clinical Use", Clinical Chemistry, vol. 32, No. 8, 1448–1459 (1986).
Fogh-Andersen, et al., "Measurement of Free Calcium Iron in Capillary Blood and Serum", Clinical Chemistry, vol. 24, No. 9, 1545–1552 (1978).
Maas, et al., "Methodology and Clinical Applications of Ion-Selective Electrodes", 4th Symposium on Ion Selective Electrodes of the International Federation of Clinical Chemistry, vol. 7, 273–279 (1986).

(List continued on next page.)

Primary Examiner—C. Warren Ivy
Assistant Examiner—Thomas McDonald, Jr.
Attorney, Agent, or Firm—Seidel, Gonda, Lavorgna & Monaco

[57] ABSTRACT

Ion selective parts are described which comprise a polymeric material, an ion selective component and optionally furthermore a plasticizer and which ion sensitive parts are suited for the determination of the concentration or activity of ions in liquid media. The polymeric material of said ion sensitive parts is a copolymer in which 5–25 mol-% of the monomeric units of said copolymer are substituted with one or more hydrophilic substituents which are selected from the group comprising hydroxy groups, carboxylic acid groups, sulphonic acid groups and phosphonic acid groups. The inventive ion selective parts have, compared with corresponding ion selective parts in which the polymeric material is free of the stated hydrophilic groups or has a lower content of said hydrophilic groups, a better stability of the standard potential $E_o$ and a lower asymmetry potential or no asymmetry potential at all. Said properties of the inventive ion selective parts are also maintained after the corresponding parts had been in contact with solutions which contain organic substances having a higher molecular weight, like proteins.

The inventive in selective parts, accordingly, can be used in apparatuses for the determination of the concentration of ions in clinical fields of application, like for instance the determination in whole blood, blood serum or blood plasma.

22 Claims, 1 Drawing Sheet

OTHER PUBLICATIONS

Walter, B., "Dry Reagent Chemistries in Clinical Analysis", *Analytical Chemistry, vol. 55, No. 4, 498–514 (1983).*

Patent Abstracts of Japan, vol. 9, No. 299 (P-408) [2022] (Nov. 27, 1985) abstracting Japanese Patent Application 60-135854 (Jul. 19, 1985).

Chemical Abstracts, vol. 90, No. 169601r, 45–46 (1979) Abstracting Japanese Patent Application 77-78, 657 (Jan. 29, 1979).

Chemical Abstracts, vol. 89, No. 148730w, 107 (1978), Abstracting Japanese Patent Application 76-73, 289 (Dec. 27, 1977).

Ladenson, J., "Ion-Selective Electrodes in Clinical Chemistry and Medicine", *Anal. Proc.*, vol. 20, 554–556 (Nov. 1983).

Patent Abstracts of Japan, vol. 11, No. 22 (p-538) [2469] (Jan. 21, 1987) Abstracting Japanese Patent Application 61-196157(A) Aug. 30, 1986).

Oesch, et al., "Membrane Technological Optimization of Ion-Selective Electrodes Based on Solvent Polymeric Membranes for Clinical Applications", 4th Symposium on Ion-Selective Electrodes, 81–101 (1984).

FIG. 1

FIG. 2

ION SELECTIVE PART OF AN APPARATUS FOR THE DETERMINATION OF THE CONCENTRATION OF IONS AND PROCESS FOR THE PREPARATION OF POLYMERIC MATERIALS CONTAINING HYDROPHILIC GROUPS

BACKGROUND OF THE INVENTION

The present invention concerns an ion selective part of an apparatus for the determination of the concentration of ions in liquid media. The ion selective part contains a polymeric material and an ion selective component having a selectivity for the ions to be determinated. The ion selective part may optionally contain a plasticizer.

Corresponding apparatuses for the determination of ion concentrations are used in many fields of the art. The polymeric material of the corresponding ion selective parts is usually polyvinylchloride. Furthermore many ion selective components having a selectivity for specific ions are described in the art. Also, several plasticizers for corresponding ion selective parts are described in publications. When the prior art apparatuses were used for the determination of the concentration of ions in aqueous media which were free of organic constituents having a comparatively high molecular weight, then usually accurate results are achieved and after a calibration of the equipment the corresponding results were also reliable and had a good reproducibility. If, however, the ion concentrations had to be determined in liquid media which contained organic constituents of comparatively high molecular weight and specially corresponding organic constituents which also comprise hydrophilic groups, such as proteins or proteinous materials, then the reproducibility of the determination of the ion concentrations was often insufficient. These deficiencies are due to the fact that the standard potential $E_o$ of the Nicolsky-Eisenmann equation shifts after the corresponding ion selective parts are in contact with the liquid medium containing proteinous materials. Furthermore, through such a contact an asymmetry potential is developed.

Since several years extended research work was done in order to find plasticizer components through which the above-stated deficiency of corresponding ion selective membranes comprising a polymeric material, an ion selective component and a plasticizer would be avoided.

It is the object of the present invention to solve the problem in a quite different way, i.e. by modifying the polymeric component of the corresponding ion selective parts so that the above stated deficiencies are avoided. It, accordingly, is the object of the present invention to provide ion selective parts which can be used in corresponding apparatuses for the determination of ion concentrations in biological material, such as body fluids, as for instance blood serum and whole blood. The corresponding ion selective parts should have a high stability of the standard potential and a low asymmetry potential or no asymmetry potential at all after they had been in contact with the corresponding liquid media containing biological constituents.

DESCRIPTION OF THE PRIOR ART

Ion selective membranes are used in many fields of the application for the determination of the concentration or the activity of several ions.

A short description of corresponding apparatuses which are used for the determination of the corresponding ions in the clinical field is given in the publication of U. Oesch, D. Ammann and W. Simon, Clinical Chemistry, vol. 32, no. 8, 1986, pages 1448–1459. In the publication also corresponding apparatuses which are suited for a clinical application, like flow-through electrodes, catheter-type electrodes, ion selective field effect transistors and slides for the potentiometric analysis are described. There is also explained that many polymeric materials have been used in combination with different plasticizers had been used for the preparation of ion selective parts. However, polyvinylchloride is by far the most commonly used polymeric component of the ion selective parts. In the publication, the requirements which have to be put to ion selective electrodes for the determination of cations and anions in whole blood, blood plasma and serum are explained, specially also with regard to the selectivity of the corresponding ion selective electrodes with regard to one specific ion over other ions present in the biological material. In said publication of the year 1986 there is furthermore emphasized on page 1450, right column, lines 17–26, that in the clinical application further properties of the ion selective parts, like stability and life time might be the failing factors. The stability is often insufficient because the standard potential is not constant, i.e. the value of $E_o$ in the Nicolsky-Eisenmann equation is shifting and a further failure that often occurs is an insufficient reproducibility of the determinated ion concentrations. In the publication there is already mentioned that there occurs a shifting of the standard potential after the ion selective part had for the first time been contacted with a protein containing solution.

Extensive efforts were undertaken to solve this problem by repeating the calibration with aqueous systems after the membrane had been in contact with the protein containing solution. With regard to this we refer to the publication of N. Fogh-Andersen, T. F. Christiansen, L. Komarny and O. Siggaard-Andersen in Clin. Chem. 1978, 24, 1545.

The shifting of the standard potential $E_o$ however is neither constant nor independent from the sample solution which had been used and therefore, the very time consuming and laborious recalibration does not yield the desired success.

Attempts were also made to solve the problem of a poorly reproducible shift of the standard potential $E_o$ of ion selective membranes comprising a polymeric material, an ion selective component and a plasticizer by applying to the ion selective part a coating of cellulose acetate, the coating on one hand will prevent an elution of the plasticizer and furthermore will prevent a deposition of proteinous materials onto the ion sensitive part. With regard to this we refer to the publication of U. Oesch, D. Ammann and W. Simon in "Methodology and Clinical Applications of Ion Selective Electrodes" and the publication of Maas, A.H.J.; Boink, F.B.T.J.; Saris, N.-E.L.; Sprokholt, R.; Wimberley, P.D., Eds.; Interprint A/S: Copenhagen, 1986, page 273 ff. Such coated ion sensitive parts, however, have drastically longer response time and, accordingly, the corresponding constant value of the determined EMF is only reached after long periods of time. This disadvantage is very detrimental if clinical field of applications are to be considered. It is desired in the clinical chemistry that a reliable value is achieved after about 30 seconds.

In the publication of U. Oesch, P. Anker, D. Ammann and W. Simon in "Ion Selective Electrodes"; Pungor, E.; Buzàs, I., Eds.; Akadémiai Kiadó: Budapest, 1985; pages 81–101, there are summarized the ion selective parts which are until now available for an application in clinical chemistry as well as also the efforts which had been undertaken to solve the stability problems.

In the publication of B. Walter in Anal. Chem. 1983, 55, pages 498A–514A, there are described apparatuses for the determination of ions and therapeutically active ingredients in the clinical field of application.

In the Japanese patent abstract, volume 11, no. 22 (P-538) [2469] of Jan. 21, 1987, there are reported the contents of the Japanese patent application No. 61-196157 of Shimadzu Corporation. According to said patent, the adverse effects due to the attaching of protein or similar substances onto an ion responsive film will be avoided. According to the process the ion responsive film is prepared by evaporating the solvent of a solution of the film so that an internal force is imparted in direction to the responsive surface of said film.

In the patent abstract of Japan, volume 9, no. 299 (P-408) [2022] of Nov. 27, 1985, which is an abstract of the Japanese patent application No. 60-135843 of Olympus Kogaku Kogyo A. K., there are described reaction films for ion selective electrodes. The films are suited for a selective and quick determination of ions, such as chloride anions in biological liquids. The corresponding copolymer film contains 10–40 mol-% of monomers having a heterocycle in the side chain such as 4-vinylpyridine, vinylacridine and vinylimidazole.

In the European patent publication No. 0 219 742 of the firm Willi Moeller, there are described shaped bodies of plastic material which have a high elasticity and highly adhesive properties and their use as ion sensitive membranes. The corresponding shaped bodies of plastic material contain as an elastifying component, high quantities of a benzophenone-tetracarboxylic acid tetraester, i.e. per 10 parts by weight of the plastic material 70–90 parts by weight of said elastifying component.

In the European patent publication No. 0 185 267 of the Teroson Company there are described plastisol compositions which are applicable by spray-coating and which are used for sound reducing purposes. The corresponding compositions contain 32–72% by weight of a vinylchloride homopolymer or a copolymer of vinylchloride and vinylacetate and, furthermore, 28–60% by weight of a mixture of at least two plasticizers and optionally furthermore a methylmethacrylate homopolymer. Accordingly, if in the compositions a vinylchloride copolymer is present then said copolymer is free of highly hydrophilic groups, e.g. hydroxy groups or, acidic groups, e.g. carboxylic acid groups.

In the publication Chemical Abstracts, volume 90, Jan. 29, 1979, pages 45+46 abstract no. 169601r, there are described hydrophilic polymers which are prepared by saponifying copolymers of hydroxyalkyl esters of unsaturated carboxylic acids and unsaturated carboxamides. The corresponding starting materials, such as the copolymer of 2-hydroxyethylmethacrylate and acrylamide, have hydrophilic properties due to the hydroxyalkyl group of the ester component and the starting material is stated to have a water absorption of 60%. After the saponification of said starting material with an aqueous ammonium hydroxide solution, there results an extremely hydrophilic polymeric material in which each monomeric constituent is substituted with a carboxylic acid group and the corresponding polymeric material is stated to have a water absorption of 617%.

The corresponding polymeric materials, accordingly, are free of any hydrophobic monomeric units, i.e. monomeric units which are free of a highly hydrophilic substituent. Furthermore, from the abstract there cannot be taken any reference for which purpose the corresponding polymeric materials with high water absorption are intended to be used.

The publication Chemical Abstracts, volume 89 of Dec. 27, 1977, page 35, abstract no. 148730w, is the abstract of the Japanese patent application No. 77,156,779 of the Asahi-Dow Limited. According to the patent, active hydrophilic membranes are prepared by using as the starting material, ethylene-vinylacetate copolymers which comprise 3–18 mol-% of vinylacetate radicals. The copolymers are shaped to membranes having a thickness of 5–100 $\mu$ which thereafter are sulphonated and saponified to yield active hydrophilic membranes which contain 0.2–4 $SO_3H$ groups, less than 4.7 OH groups and wherein there remain in the membrane not saponified acetic ester groups in a quantity of 0.1 molar equivalents per gram. There is stated that the resulting membranes have a water absorption in the range of 10–200% and a high ion exchange capacity. The corresponding membranes are used for performing electrolysis and dialyses.

In spite of the intensive research work performed in the field, it was not until now possible to provide ion selective parts which have a high stability of the standard potential $E_o$ of the Nicolsky-Eisenmann equation and a low asymmetry potential or no asymmetry potential at all after they have been contacted with a sample solution which contains organic constituents having a higher molecular weight and comprising hydrophilic groups e.g. proteins. Laborious and very time consuming recalibrations had been made after the ion selective parts had been in contact with a sample solution containing proteinous material. The recalibrations were performed with aqueous solutions and even with protein containing solutions (see the publication of J. H. Ladenson in Analytical Proceedings 1983, volume 20, page 554). As, however, the shifting of the standard potential $E_o$ is dependent from the sample solutions with which the ion selective part had been in contact, even with the laborious methods the problem could not be solved until now.

DESCRIPTION OF THE INVENTION

It is the object of the present invention to investigate whether through a modification of the polymer component of an ion selective part of an apparatus for the determination of the concentration of ions in liquid media it perhaps would be possible to provide ion selective parts which do not have the above stated disadvantages of corresponding prior art ion selective parts containing a polymeric component, the ion selective component and optionally furthermore a plasticizer.

Quite unexpectedly it was found out that ion selective parts which meet the necessary requirements can be prepared by using a polymeric material, which comprises in addition to monomeric units which have no hydrophilic properties also a smaller amount of monomeric units which are substituted with hydrophilic substituents which are selected from the group comprising hydroxy groups, carboxylic acid groups, sulphonic acid groups, phosphonic acid groups or two or more of the stated hydrophilic groups.

One subject of the present invention, accordingly, is an ion selective part of an apparatus for the determination of the concentration of ions in liquid media, which ion selective part comprises a polymeric material and an ion selective component having a selectivity for the ions, the concentration of which is to be determined, and the ion selective part is characterized in that the polymeric material is a copolymer which is derived from monomeric units which are unsubstituted alkenes or unsubstituted alkynes having one or more double bonds, respectively triple bonds, or substituted alkenes or substituted alkynes having one or more double bonds or triple bonds wherein the susbstituents are selected from the group which comprises halide atoms, aryl groups, carboxylic acid ester groups, carboxylic acid amide groups, nitrilo groups, sulfonic acid ester groups, sulfonamide groups, phosphonic acid ester groups, phosphonic acid amide groups, esterified or etherified hydroxy groups, keto groups, free or acetalized aldehyde groups, and/or wherein in the polymeric chain of the copolymer there are either present no groups which interrupt the carbon chain or there are present also polyester moieties, polyether moieties, polyurethane moieties, polyamide moieties, polycarbonate moieties, or two or more of said moieties and wherein 5-25 mol-% of the monomeric units of said copolymer are substituted with one or more hydrophilic substituents which are selected from the group comprising hydroxy groups, carboxylic acid groups, sulphonic acid groups, phosphonic acid groups or two or more of the stated hydrophilic groups and wherein the ion selective parts have a higher stability of the standard potential $E_o$ of the Nicolsky-Eisenmann equation and the lower asymmetry potential or no asymmetry potential, compared with corresponding ion selective parts, the polymeric material of which comprises less than 5% of monomeric units which are substituted with the hydrophilic substituents or which polymeric materials are free of monomeric units which are substituted with the stated hydrophilic substituents.

Preferably the polymeric component of the inventive ion selective part is a corresponding copolymer having a carbon chain background which is not interrupted by any ether groups, ester groups, amide groups, urethane groups or carbonate groups.

Preferred are furthermore such copolymer components in which the hydrophobic monomeric units of the copolymer are other monomeric units than those of unsubstituted ethylene.

As already mentioned before in the European patent publication No. 0 219 742 of Moeller which corresponds to the not yet published U.S. patent application Ser. No. 914,390 of W. Simon, there are described shaped bodies of plastic material which have a high elasticity and highly adhesive properties and which contain large quantities of a benzophenone tetracarboxylic acid tetraester. There is mentioned in the European patent publication that the polymeric component of the shaped bodies is preferably a polyethylene, a polypropylene, a polyvinylhalide, a polystyrene, a polyester, a polyamide, a polyacrylnitrile, a polyurethane, a polycarbonate, a polyvinylidenehalide or a copolymer of two or more such monomeric units. It, furthermore, is mentioned in the European patent publication that the monomeric units of the plastic component optionally can also comprise small amounts of monomeric components having more hydrophilic properties, like monomeric units which have substituents which are hydroxy groups, ester groups or optionally carboxylic acid groups. From the European patent publication, however, there is no reference that the polymeric component which comprises some hydrophilic groups has any advantages over the corresponding polymeric component which is free of hydrophilic groups. In the examples of the European patent publication there are only described corresponding highly elastic and tacky plastic compositions in which polyvinylchloride is combined with the benzophenone tetracarboxylic acid tetraester-plasticizer.

If in the inventive ion selective parts the polymeric material is a copolymer of polyvinylchloride and polyvinylalcohol, in which copolymer 5 mol-% of the monomeric units are derived from vinylalcohol, then the corresponding product, accordingly, comprises: 95 mol-% of polyvinylchloride having a molecular weight of 62.5 and 5 mol-% of polyvinylalcohol having a molecular weight of 44, so that the average molecular weight of the total monomeric units of the copolymer is 61.57. The content of hydroxy groups in the copolymer is accordingly 1.38% by weight.

If in the inventive ion selective part the polymeric material is a copolymer of polyvinylchloride and an unsaturated carboxylic acid having the formula $C_2H_3$—COOH and if in the copolymer 5 mol-% of the monomeric constituents are derived from the monomeric constituents of the stated monocarboxylic acid, which has a molecular weight of 72.06, then the copolymeric product has an average molecular weight of all its monomeric units of 63.0. Based on the average molecular weight, accordingly, the content of the copolymeric material of groups of formula —COOH is 3.57% by weight.

A polyvinylchloride which has carboxylic acid substituents, however, far less than the above mentioned % by weight, i.e. only a content of groups of formula —COOH of 1.7% by weight, is a product which is sold by the Aldrich company. The polyvinylchloride with only a few carboxylic acid substituents now was reduced and thereby a hydroxy substituted polyvinylchloride was prepared, the oxygen content of which was 0.7% by weight. The preparation of the hydroxy substituted polyvinylchloride is described in the publication of Trevor Satchwill and D. Jed Harrison in J. Electroanal. Chem. 202 (1986), pages 75–81. In the publication there are furthermore described ion selective membranes which contain an ion selective component, a plasticizer and furthermore a polymeric component which is a polyvinylchloride copolymer containing either the above stated low quantity of polymeric units which are derived from the hydroxy substituted monomeric constituents or the low quantities of the above mentioned carboxylic acid substituted monomeric units. It is furthermore explained in the publication that the corresponding ion selective membranes have a far better adherence onto surfaces of silicondioxide than corresponding membranes the polymeric component of which is a corresponding not modified polyvinylchloride homopolymer. In the publication there are to be found furthermore calibration curves from which there can be seen that the electrochemical properties of the corresponding membranes containing the modified polyvinylchloride copolymer are identical or nearly identical with the electrochemical properties of corresponding membranes containing the not modified polyvinylchloride homopolymer. Accordingly, from the publication there can be seen that the substitution of polyvinylchloride homopolymer by polyvinylchloride copolymers which have a very low content of polymeric units derived from monomeric units which are substituted with hydroxy groups or carboxylic acid groups, does not alter the electrochemical properties of the corresponding membrane.

In order to show that the advantages of the inventive ion selective parts can be only achieved if at least 5 mol-% of the monomeric units of the polymer are substituted with one or more of the stated hydrophilic substituents, there were performed tests for comparison. For the purpose there were prepared polymeric components which were polyvinylchloride copolymers in which, however, only 3 mol-% of the monomeric units were derived from polyvinylalcohol, respectively of the unsaturated monocarboxylic acid having the formula $C_2H_3$—COOH. Ion selective parts for comparison were prepared using the polymeric components and after said ion selective parts had been contacted with a protein containing test solution they showed no better stability or nearly no better stability of the standard potential than corresponding ion selective parts in which the polymeric material was a not modified polyvinylchloride which was completely free of any hydrophilic groups.

The polyvinylchloride copolymer in which only 3 mol-% of the monomeric units are derived from polyvinylalcohol which polymeric material was used in the above stated test for comparison, has about the same low content of hydroxy groups as the polyvinylchloride copolymer which is described in the above stated publication of Trevor Satchwill et al. The two polyvinylchloride copolymers with the too low content of hydroxy groups, however, differ from each other as to their chemical structure. In the polyvinylchloride copolymer described in the publication the hydroxy groups were produced through a reduction of carboxylic acid groups and accordingly to the carbon chain of the polymeric material there are bonded groups of formula —$CH_2$—OH. Contrary to this, the polyvinylchloride copolymer of the tests for comparison comprises monomeric units which are derived from polyvinylalcohol and therefore in said polymer the hydroxy groups are directly bonded to the carbon chain of the polymeric material.

The tests for comparison which were performed, accordingly, demonstrate that it is essential that the polymeric component of the inventive ion selective parts contains a sufficient amount of hydrophilic substituents. If in the corresponding copolymer clearly less than 5% of the monomeric units are monomeric units which contain hydrophilic substituents selected from the group comprising hydroxy groups, carboxylic acid groups, sulfonic acid groups and phosphonic acid groups, then the ion selective parts prepared using such a polymeric material do not have the advantages of the inventive ion selective parts as to the stability of the standard potential and as to the development of no asymmetry potential. On the other hand it also is essential that not more than 25 mole-% of the monomer units of the copolymer are derived from the monomers containing said hydrophilic substituents because at higher contents of hydrophilic groups the corresponding ion selective membranes exhibit too strong hydrophilic characteristics.

The inventive ion selective parts are suited for a determination of the activity of concentration of ions in such liquid media which contain as further components organic material, and preferably organic substances having a rather high molecular weight and, furthermore, hydrophilic groups such as proteins and similar biological materials. When the inventive ion selective parts are contacted with sample solutions containing said further constituents then a good stability of the standard potential $E_o$ of the Nicolsky-Eisenmann equation is provided. Accordingly, no shifting or drifting of said standard potential $E_o$ is to be observed. Because of this the time consuming and laborious recalibration of the equipment either with aqueous solutions or with protein containing solutions is avoided.

A further advantage of the inventive ion selective parts is the short response time. Accordingly, if with an apparatus equipped with the inventive ion selective part the concentration, respectively activity, of a certain kind of ions is determined in a sample solution by a determination of the EMF of the corresponding electrode system, then very soon after the contact with the sample solution the EMF has reached a constant value which is determinated. As already outlined before, short response times are of decisive importance if the corresponding ion selective part will be used in the field of clinical chemistry and neurophysiological laboratories. Quite surprisingly the response times of inventive ion selective parts is far shorter than the response time of until now used ion selective parts, the polymeric component of which was free of hydrophilic groups, if the ion concentrations are determined in test solutions containing proteinous materials.

In the field of the determination of concentrations or activities of cations or anions, it is well known to establish calibration curves and in said graphs there are usually plotted on the ordinate the determinated EMF values in millivolts and on the abscissa there is plotted the logarithm of the concentration respectively activity of the anion or cation to be determinated. The slope of the electrode response of electrodes equipped with inventive ion selective parts and corresponding electrodes equipped with prior art ion selective parts the polymeric component of which is free of hydrophilic groups, is nearly identical. With regard to this we once more refer to the Nicolsky-Eisenmann equation and the explanations given with regard to said Nicolsky-Eisenmann equation in the already named publication of U. Oesch in Clinical Chemistry, vol. 32, no. 8 (1986), pages 1448-1459.

With regard to said Nicolsky-Eisenmann equation, we, furthermore, want to draw your attention to the publication "Calcium-selective electrodes" of W. Simon, D. Ammann, M. Oehme and W. E. Morf in Annals of the New York Academy of Sciences, vol. 307, pages 52-70, Apr. 28, 1978. In the publication there is explained for the calcium ion that the Nicolsky-Eisenmann equation reduces to the following simplified form provided that in the sample solution the determination of the calcium ions is not interfered by any other ions present in the sample.

$$E_{Ca} = E^o{}_{Ca} + s \cdot \log a_{Ca}.$$

In said equation $E^o{}_{Ca}$ is the standard potential $E_o$ for the calcium ions $a_{Ca}$ is the activity of the calcium ion in the sample solution and $s$ is the slope of the electrode response function.

A further advantage of the inventive ion selective parts is that their electrical resistance is far lower, compared with the electrical resistance of corresponding ion selective parts, the polymeric component of which is free of hydrophilic groups.

Furthermore, the inventive ion selective parts, for example corresponding ion selective membranes, have a better adherence to substrates, compared with the adherence of corresponding ion selective parts, the polymeric material of which is free of hydrophilic substituents. Such an improved adherence is to be observed on substrates of silicon containing materials such as glass, quartz glass and silicone resins.

The copolymers contained in the inventive ion selective parts and also the corresponding ion selective parts only absorb a small amount of water. In general, the corresponding copolymers have a water absorption of less than 10% by weight relative to the total weight of the copolymer and the absorbed water, and preferably this water absorption amounts only to 8% by weight or even less.

Preferred inventive ion selective parts contain as polymeric material a polyvinylhalide copolymer or a polyvinylidenehalide copolymer, in which 5 to 25 mol-% of the monomeric units are substituted with the stated hydrophilic substituents and wherein the copolymer is free of any further substituents or comprises further substituents which are selected from the group comprising ester groups, acid amide groups, nitrilo groups, carbonate groups and/or urethane groups. Of the stated polyvinylhalide copolymers and polyvinylidenehalide copolymers respectively, those are preferred in which the hydrophilic groups are hydroxy groups and/or carboxy groups. The preferred halide atom of said copolymers is the chloride.

It was already pointed out that the advantages of the inventive ion selective parts can be only achieved if the polymer component thereof is a copolymer in which 5 to 25 mol-% of the monomeric units thereof are substituted with one or more hydrophilic substituents which are selected from the group comprising hydroxy groups, carboxylic acid groups, sulfonic acid groups, phosphonic acid groups or two or more of the stated hydrophilic groups. Preferred are, however, such copolymers in which 7.0-18.2 mol-% of the monomeric units of the copolymer are substituted with one or more hydrophilic substituents which are selected from the group comprising hydroxy groups, carboxylic acid groups, sulfonic acid groups, phosphonic acid groups or two or more of the stated hydrophilic groups. Specially preferred are such copolymers in which 10.9–13.8 mol-% of the monomeric units are substituted with the above named hydrophilic substituents.

The preferred polymeric material of the inventive ion selective parts is a copolymer of vinylchloride and vinylalcohol, a copolymer of vinylchloride and an unsaturated monocarboxylic acid or polycarboxylic acid or a copolymer of vinylchloride, vinylalcohol and an unsaturated monocarboxylic acid or polycarboxylic acid and in the copolymer 5-25 mol-% of the monomeric units of the copolymer have to be derived from polyvinylalcohol and/or the unsaturated monocarboxylic acid or polycarboxylic acid. The corresponding copolymers can be free of further substituents or they can contain further substituents selected from the group comprising carboxylic acid ester groups, carboxylic acid amide groups and nitrilo groups, preferably esterified hydroxy groups or esterified carboxylic acid groups.

Also in the preferred copolymers of vinylchloride and vinylalcohol and/or unsaturated monocarboxylic acids or polycarboxylic acids, it is preferred if 7.0-18.2 mol-% of the monomeric units of said copolymer are derived from the vinylalcohol and/or the unsaturated monocarboxylic acids or polycarboxylic acids. Specially preferred are such copolymers wherein 10.9-13.8 mol-% of the monomeric units are derived from vinylalcohol and/or the unsaturated monocarboxylic acids or polycarboxylic acids.

The inventive ion selective parts can be prepared without the use of plasticizers, because, in comparison with ion selective parts, wherein the polymer component is free of hydrophilic substituents, they show stronger hydrophilic characteristics and also a good adhesion on substrates.

Contrary to this fact the ion selective parts known in the prior art which have a polymer component which is free from any hydrophilic substituents, practically always contained as further component a plasticizer, because otherwise the hydrophilic characteristics of the composition of ion sensitive parts and hydrophobic polymer material would be inadequate.

But frequently also the inventive ion selective parts contain additionally to the ion selective component a plasticizer. In this case the corresponding ion selective parts preferably have the following composition:

If, however, the inventive ion selective parts contain a plasticizer, then they usually have the following composition:

0.5–5% by weight of the ion selective component

30–50% by weight of the copolymer comprising the stated amount of hydrophilic groups and 50–70% by weight of a plasticizer.

Corresponding inventive ion sensitive parts, in which the polymeric component is a polyvinylchloride containing hydrophilic groups, usually have the following compositions:

0.5–1% by weight of the ion selective component

30–36% by weight of the polyvinylchloride copolymer comprising hydrophilic groups, 64–70% by weight of a plasticizer.

Typical examples for plasticizers used in ion selective parts are ester plasticizers such as diesters of dicarboxylic acids, e.g. corresponding esters of the adipic acid or the sebacic acid with alkanols of about 8 carbon atoms.

The ion selective component of the inventive ion selective part can be any ion selective component which has the desired selectivity for the ion to be determined over other kinds of ions which will be present in the sample solution. For instance, if potassium ions will be determined then the ion sensitive component of the membrane will usually be valinomycin.

Further ion sensitive components for the determination of calcium ions, sodium ions, lithium ions are well known in the art, some of them in detail will be defined later.

However, the ion sensitive component also can be an ion sensitive component for the determination of concentrations and the activity of anions. A typical example is the determination of carbonate anions or of anions of oxa acids, e.g. sulfates or carboxylic acids.

Independently from the used ion sensitive component the inventive ion selective parts have the advantage of a constant, i.e. non shifting standard potential and the absence of an asymmetry potential if they are compared with corresponding ion sensitive parts, the polymeric component of which is free of hydrophilic groups or has a lower or higher content of hydrophilic groups than the polymeric material of the inventive ion sensitive members.

It is possible to use the inventive ion selective part in different apparatuses for the determination of the concentration of ions in sample solutions, such as the determination of cations and anions in body fluids. The corresponding ion sensitive parts can be the ion sensitive membranes of ion sensitive electrodes, for instance flow-through electrodes or electrodes of the catheter type. Furthermore, corresponding ion sensitive membranes can be contained in slides for the performance of potentiometric analyses or the membranes of ion selective field effect transistors.

The inventive ion selective parts can be also the corresponding ion sensitive parts of small systems with which not only the concentration or activity of one ion but of several ions is tested. In such miniaturized systems ion selective regions which have a selectivity for different kinds of ions, are situated in neighboring regions of said miniaturized systems.

Minielectrodes in which the inventive ion selective parts can be used are furthermore described in the publication of R. E. Dohner, D. Wegmann, W. E. Morf and W. Simon in Analytical Chemistry, volume 58, 1986, pages 2585-2589.

A further field of application of the inventive ion sensitive parts are ion selective coatings of electrical conductors, i.e. the so called coated wire-electrodes. Electrodes of the kind are described in the corresponding passage of the book "Ion Selective Electrodes in Analytical Chemistry", volume 2, of Henry Freiser, edited by Plenum Press, New York and London, 1980.

As already stated before the inventive ion sensitive parts are specially advantageous over prior art ion selective parts in those fields of the application, where the corresponding ion selective parts come into contact with sample solutions containing comparatively high molecular weight organic materials or biological materials, such as proteins or carbohydrates of high molecular weight, e.g. products which are obtained when starch or cellulose materials are submitted to incomplete hydrolysis. Apparatuses equipped with the inventive ion selective parts therefore can be used for the determination of any kind of cations or anions in liquid sample solutions which contain the organic constituents of higher molecular weight. Examples for such sample solutions are product streams which have to be analyzed in the course of an industrial preparation of several chemical products or biochemical products or food stuffs such as of the preparation of different pharmaceutically active ingredients, dyestuffs, starch derivatives, cellulose derivatives and products prepared through fermentation processes. A further important field of application is the determination of the concentration, respectively activity of different kinds of ions in liquid samples of waste material which samples, furthermore, contain the organic materials of higher molecular weight, e.g. a determination of the ions in waste water.

Furthermore, it is advantageous to equip such apparatuses which are used for the determination of the concentrations of ions in body fluids with inventive ion selective parts. Examples for such apparatuses are clinical apparatuses for the determination of ions in whole blood, blood serum or blood plasma or for the determination of ions in urine. If the corresponding apparatuses are equipped with inventive ion sensitive parts then a very rapid and reliable determination of different ions is possible in the clinical field, like for instance the determination of lithium, sodium, potassium, calcium, carbonate, anions of oxygen containing acids, such as organic acids, sulphuric acid, and also the determination of oxygen present in the liquid materials.

It is advantageous if the polymeric component of the inventive ion sensitive parts has a high molecular weight and preferably the molecular weight of the corresponding copolymer should be at least 10,000. Still more preferred are corresponding copolymers which have a molecular weight of at least 40,000 and more preferred at least 50,000, like e.g. a molecular weight of 90,000 or higher. The K-value of the polymeric materials is usually more than 50.

The polymeric component of the inventive ion selective parts can be prepared according to any one of the well known processes for preparing polymeric materials on principle, e.g. by a polymerization of the corresponding monomeric materials.

More advantageous, however, it is usually to prepared the polymeric component of the inventive ion sensitive parts by using as starting material a copolymer in which the hydrophilic groups of the final copolymer, which hydrophilic groups are selected from the group comprising hydroxy groups, carboxylic acid groups, sulfonic acid groups, phosphonic acid groups or two or more of the stated hydrophilic groups, are present in a protected form.

A further object of the present invention, accordingly, is a corresponding process for the preparation of the copolymer component of the inventive ion selective part.

A further object of the present invention, accordingly, is a process for the preparation of a copolymer which comprises monomeric units which are derived from unsubstituted alkenes or unsubstituted alkynes having one or more double bonds, respectively triple bonds, or from substituted alkenes or substituted alkynes having one or more double bonds or triple bonds, wherein the substituents are selected from the group which comprises halide atoms, aryl groups, carboxylic acid ester groups, carboxylic acid amide groups, nitrilo groups, sulfonic acid ester groups, sulfonic acid amide groups, phosphonic acid ester groups, phosphonic acid amide groups, esterified or etherified hydroxy groups, keto groups, free or acetalized aldehyde groups, and in which copolymer there are either present no groups which interrupt the carbon chain or there are present ether or polyether moieties, ester or polyester moieties, urethane or polyurethane moieties, amide or polyamide moieties, carbonate or polycarbonate moieties or two or more of said moieties, which interrupt the carbon chain of the backbone of the copolymer and in which copolymers.

5-25 mol-% of the monomeric units of the copolymer are substituted with one or more hydrophilic substituents which are selected from the group comprising hydroxy groups, carboxylic acid groups, sulfonic acid groups, phosphonic acid groups or two or more of the stated hydrophilic groups, and wherein the inventive process for the preparation of the copolymers as characterized in that a corresponding homopolymer or copolymer in which the hydroxy groups are present in the form of their esters, carboxylic acid groups, sulfonic acid groups and/or phosphonic acid groups are present in the form of their esters, in the form of acid amides or as nitrile, is submitted to a saponification in order to convert the stated groups into free hydroxy groups, carboxylic acid groups, sulfonic acid groups, respectively phosphonic acid groups and wherein the saponification is allowed to proceed until in the copolymer 5-25 mol-% of the monomeric units are monomeric units which are substituted with one or more hydrophilic substituents which are selected from the group which comprises hydroxy groups, carboxylic acid groups, sulfonic acid groups, phosphonic acid groups or two or more of the stated hydrophilic groups.

For example in the corresponding copolymer starting materials the hydroxy groups can be present in the form of esters with organic acids, for instance lower aliphatic carboxylic acids, like alkane carboxylic acids comprising totally 2-5 carbon atoms. Specially preferred ester protective groups are the corresponding acetates.

If in the starting materials the carboxylic acid groups, sulfonic acid groups and/or phosphonic acid groups are present in the form of their ester then preferred ester protective groups are the lower alkyl esters having 1-6 carbon atoms in the alkyl groups, e.g. the methyl esters, ethyl esters, n-propylesters or isopropylesters. Suitable protective groups for the carboxylic acid groups, sulfonic acid groups, respectively phosphonic acid groups, are furthermore the corresponding acid amide groups, and preferred amino components which form the acid amides are ammonia, lower monoalkyl amines or lower dialkyl amines. In as far as carboxylic acid groups are concerned the corresponding protected carboxylic acid group can also be a nitrilo group.

If a polymeric material is prepared in which the corresponding hydrophilic groups are hydroxy groups and furthermore carboxylic acid groups or hydroxy groups and sulfonic acid groups or hydroxy groups and phosphonic acid groups, then the corresponding protected form of the kinds of groups can also be an inner ester between the hydroxy groups and the stated acid groups. Accordingly, if a polymeric material has to be prepared in which the hydrophilic groups are hydroxy groups and carboxylic acid groups then the inner ester can be a cyclic lactone. If a corresponding homopolymer or copolymer which has in its polymeric structure said lactone groups is submitted to the saponification then each saponified lactone group yields a free hydroxy group and, furthermore also a free carboxylic acid group.

According to a preferred embodiment of the inventive process there is prepared a polyvinylhalide copolymer or a polyvinylidenhalide copolymer in which copolymer 5-25 mol-% of the monomeric units are substituted with one or more hydrophilic substituents, which are selected from the group comprising hydroxy groups, carboxylic acid groups, sulfonic acid groups, phosphonic acid groups or two or more of the stated hydrophilic groups, and wherein from a corresponding polyvinylhalide copolymer, respectively polyvinylidenehalide copolymer, in which the hydroxy groups are present in the form of their esters and the carboxylic acid groups, sulfonic acid groups and/or phosphonic acid groups are present in the form of their esters or in the form of their acid amides, is submitted to a saponification through which the corresponding hydroxy groups, carboxylic acid groups, sulfonic acid groups, respectively phosphonic acid groups, are set free, and wherein the saponification of the vinylhalide copolymer, respectively vinylidenehalide copolymer, is allowed to proceed until the mol-% of the monomeric units which are substituted with one of the stated hydrophilic substituents, are in the range of 5-25 mol-%, referred to the monomeric units of the copolymer.

Preferred polyvinylhalide copolymers, respectively polyvinylidenehalide copolymers, prepared according to the process are the corresponding polyvinylchloride copolymers, respectively polyvinylidenechloride copolymers.

According to a preferred embodiment of the above stated process the saponification reaction is allowed to proceed until a vinylhalide copolymer or vinylidenhalide copolymer is produced in which 7.0 to 18.2 mol-%, preferably 10.9 to 13.8 mol-% of the monomeric units are monomeric units which are substituted with one or more of the hydrophilic groups which are selected from the group comprising hydroxy groups, carboxylic acid groups, sulfonic acid groups, phosphonic acid groups or one or more of said hydrophilic groups.

According to a preferred embodiment of the process a copolymer of vinylchloride and vinylalcohol or a copolymer of vinylchloride, vinylalcohol and vinylacetate is prepared in which 7.0-18.2 mol-% of the monomeric units of the copolymer are vinylalcohol units and in which copolymer preferably 10.9-13.8 mol-% of said monomeric units are vinylalcohol units. According to the process a copolymer of vinylchloride and vinylacetate, in which at least 7.0 mol-% of the monomeric units are vinylacetate units, is submitted to a saponification through which the acetate groups are converted to hydroxy groups and wherein the saponification reaction is allowed to proceed until in the resulting copolymer 7.0-18.2 mol-% of the monomeric units are monomeric units derived from vinylalcohol, preferably until in the resulting copolymer 10.9-13.8 mol-% of the monomeric units are monomeric units derived from vinylalcohol.

The inventive ion selective parts are preferably prepared by dissolving the copolymer and the ion selective components and optionally furthermore a plasticizer in a volatile organic solvent and by casting said solution and letting the solvent evaporate until there remains the corresponding solvent free ion selective part.

It was found out that it is specially advantageous if the solvent is evaporated very slowly. Probably through the slow evaporation of the solvent there is prevented that surface areas of the cast shaped body or membrane are already rather poor in solvent, while in the inner parts of the cast shaped body or membrane there are still present higher contents of the volatile solvent. Probably also through a very slow evaporation of the volatile solvent a better orientation of the polymeric chains in the copolymeric component of the corresponding shaped bodies is achieved.

The very slow evaporation of the solvent is of importance if ion selective parts are prepared in which the corresponding copolymer component has a high molecular weight, preferably a molecular weight of at least 40,000 and still more preferred a molecular weight of at least 90,000 or higher.

If ion selective parts are prepared using the copolymeric component of a high molecular weight it is specially preferred to cast the corresponding ion selective parts and to maintain an atmosphere over the cast shaped body which is at the beginning saturated with the volatile organic solvent. Gradually then the content of the atmosphere in the volatile solvent is reduced until within about 2-6 days, e.g. after about four days, the atmosphere over the cast shaped body is free of any solvent and there remains a completely solvent free ion sensitive part.

The present invention will be further illustrated by the following not limitative examples.

EXAMPLE 1

Preparation of a Copolymer of Vinylalcohol and Vinylchloride

The starting material for the preparation of the copolymer was a copolymer of the following monomeric constituents:
81% by weight of vinylchloride
17% by weight of vinylacetate and
2% by weight of maleic acid.

The corresponding starting material is available in the market from the Scientific Polymer-Products Inc., Ontario N.Y., U.S.A.

5 g of the copolymer were dissolved in 100 ml of tetrahydrofuran and the solution was stirred and drop by drop to the stirred solution there was added a solution of 30 ml of a methanolic sodium hydroxide solution during ten minutes. The methanolic sodium hydroxide solution contained 1% by weight of NaOH and said methanolic solution had been warmed to a temperature of 50°-60° C.

After all of the methanolic sodium hydroxide solution had been added the tetrahydrofuran solution was stirred for 1½ hours at a temperature of 63° C. and then about half of the quantity of the added methanol was evaporated.

The remaining reaction material was filtered through a paper filter and the filtrate poured into 1.5 liters of vigorously stirred water having a temperature of 25° C.

The copolymer precipitated and after about ten minutes said precipitate was removed by filtration and suspended in 300 ml of methanol and thereafter once again removed by filtration. The filter cake was once again suspended in 200 ml of methanol and thereafter stirred into 0.8 l of water having a temperature of 25° C.

The solid materials were filtered off and dried under vacuum at a temperature of 60° C. A yield of 1.2 g of the copolymer of vinylalcohol and vinylchloride was obtained.

The IR spectrum of the polymer showed that the sharp signal at 1731 $cm^{-1}$ due to the CO stretching vibration of the acetate group of the starting material had disappeared. The IR spectrum of the produced copolymer of vinylalcohol and vinylchloride showed after said complete saponification of all the acetate groups the broad OH signal at 3400 $cm^{-1}$.

Under the applied reaction conditions accordingly all the acetate groups of the starting material had been saponified yielding hydroxy groups and, accordingly, the produced copolymer of vinylchloride and vinylalcohol consisted of 87.7 mol-% of vinylchloride plus 12.3 mol-% of vinylalcohol.

EXAMPLE 2

Preparation of a Copolymer of Vinylalcohol and Vinylchloride

The starting material for the preparation of said copolymer was a copolymer of 82.9% by weight of vinylchloride and 17.1% by weight of vinylacetate.

Due to the molecular weight of the vinylchloride of 62.5 and the molecular weight of the vinylacetate of 86.09, the molar composition of the copolymer used as starting material was 86.975 mol-% of vinylchloride and 13.025 mol-% of vinylacetate.

5 g of the copolymer were saponified according to the process described in example 1.

The saponification yielded 1.2 g of a copolymer of vinylalcohol and vinylchloride.

The IR spectrum showed that through the saponification all acetate groups had been converted to hydroxy groups. The sharp signal of the starting material at 1731 $cm^{-1}$ of the acetate groups had disappeared and the product showed a broad OH signal at 3400 $cm^{-1}$.

The corresponding copolymer, accordingly, contained 87.0 mol-% of vinylchloride plus 13.0 mol-% of vinylalcohol.

EXAMPLE 3

Preparation of Ion Selective Membranes

The inventive ion selective membranes were prepared using the polymeric materials prepared according to example 1 and example 2, i.e. the corresponding copolymers of vinylchloride and vinylalcohol.

In the tests for comparison the membranes were prepared using as polymeric component a polyvinylchloride which was free of any hydrophilic substituents. This corresponding polyvinylchloride was a product sold by the Fluka Company, CH 9470 Buchs, Switzerland, and the product is designated by the company as "PVC-hochmolekular, Fluka No. 81392".

Inventive membranes and membranes for the tests for comparison were prepared which contained the following components:
1% by weight of the ion selective component
66% by weight of the dicarboxylic acid diester plasticizer and
33% by weight of the polymeric component.

The used dicarboxylic acid diester plasticizer was bis(1-butylpentyl)adipate.

The ion selective component of the membranes for the determination of the concentration or activity of the calcium ions was the diethyl-N,N'-[(4R,5R)-4,5-dimethyl-1,8-dioxo-3,6-dioxaoctamethylene] bis (12-methylamino-dodecanoate, i.e. the dicarboxylic acid diamide of the structure 12, which is already described in the publication of U. Oesch, P. Anker, D. Ammann and W. Simon in "Ion Selective Electrodes"; Pungor, E.; Buzàs, I., Eds.; Akadémiai Kiadó: Budapest, 1985.

Contrary to the composition of all other ion selective membranes the inventive membrane for the determination of the concentration of the calcium ions and also of the corresponding membranes for comparison, had a somewhat different composition, because said membranes contained as further component the potassium-tetrakis-parachlorophenyl borate.

The composition of said calcium selective membranes was as follows:
3.3% by weight of the ion selective components
2.1% by weight of the potassium-tetrakis-parachlorophenyl borate
63.7% by weight of the dicarboxylic acid diester softener
30.9% by weight of the polymeric material.

For the preparation of one group of the membranes for the determination of the concentration, respectively activity, of sodium ions there was used as ion selective component the N,N'-dibenzyl-N,N'-diphenyl-1,2-phenylene-dioxidiacetamide, i.e. a compound having the structure 5 named on page 101 of the above stated publication.

In the second group of ion selective membranes for the determination of the concentration or activity of sodium ions there was used as ion selective component the N,N,N',N'-tetracyclohexyl-1,2-phenylene-dioxydiacetamide. In the dicarboxylic acid diamide, accordingly, the amide forming amine is dicyclohexylamine.

The ion selective component for the membranes for the determination of the concentration, respectively activity, of potassium ions was valinomycine.

The preparation of the membranes was performed according to the process described in the publication of R. Dohner, D. Wegmann, W. E. Morf and W. Simon in Anal. Chem. 1986, 58, pages 2585-2589, and in the publications cited therein.

When as plastic component, the copolymer of polyvinylchloride and polyvinylalcohol was used as described in example 2 then as solvent for casting the membranes there was used tetrahydrofuran and the solvent was evaporated very slowly during four days according to the process described before.

The inventive membranes had a better adherence to substrates e.g. substrates of silicon dioxide containing materials, such as glass, quartz glass and silicone resin, then corresponding membranes for comparison which contained as polymeric component the polyvinylchloridehomopolymer. The water absorption of the inventive membranes was below 10% by weight, usually less than 8% by weight.

EXAMPLE 4

Conditioning of the Inventive Membranes and the Membranes for Comparison

The membranes were mounted in an apparatus so that it was possible to bring each of the two surfaces of the membranes into contact with solutions having a different composition. One of the two surfaces of the membrane was contacted with a corresponding electrolyte solution and the other surface of the membrane was contacted either with a 7% bovine serum albumin solution in a 0.9% by weight physiological brine solution (the solution in the future will be named BSA-solution) or the surface of the membrane was contacted instead of this with a 6% by weight human serum albumin solution in a 0.9% by weight physiological brine solution and the solution in the future will be named HSA-solution.

The bovine serum albumin used is the corresponding product available from the Fluka Company, CH-9470 Buchs, Switzerland, and the human serum albumin solution used was available from the Swiss Central Laboratory for Blood Transfusion, Organization of the Red Cross, Switzerland.

The conditioning of both sides of the membrane was performed at the same time during 24 hours. After said conditioning both sides of the membranes were washed several times with the electrolyte solution and after the washing procedure the asymmetry potential of the corresponding inventive membranes and the membranes for comparison was determined.

EXAMPLE 5

Electrode Systems with which the Measurement of the Asymmetry Potential was Performed For the determination of the asymmetry potential of the inventive membranes and the membranes for comparison a cell of the following type was used:

Hg; $Hg_2Cl_2$, KCl (sat.)|0.1M KCl|electrolyte solution||membrane||electrolyte solution|0.1M KCl|KCl (sat.), $Hg_2Cl_2$; Hg.

When the inventive calcium selective membranes and the calcium selective membranes for comparison were tested the electrolyte solution was a 0.1 molar solution of $CaCl_2$. When the inventive sodium selective membranes and the sodium selective membranes for comparison were tested then the electrolyte solution was a 0.1 molar solution of sodium chloride.

When the inventive potassium selective membranes and the potassium selective membranes for comparison were tested then the electrolyte solution was a 0.1 molar solution of potassium chloride.

When the asymmetry potential is determined then it is essential that the test cell has the completely symmetric structure stated before.

The inventive calcium selective membranes and also the corresponding membranes for comparison in which the polymeric component was the polyvinylchloride which was free of any hydrophilic groups, were electrically symmetric after both sides of the membranes had been contacted with a corresponding electrolyte solution for 24 hours or for 48 hours. As already explained here the aqueous electrolyte solutions used for the conditioning were 0.1 molar solutions of calcium chloride.

Thereafter further conditioning experiments were performed, however now one side of the calcium selective membrane was brought into contact with the 7% by weight BSA-solution and the other side of the membrane was contacted with the 0.1 molar solution of calcium chloride.

In the experiments the membranes for comparison had at the beginning an asymmetry potential of more than 5 mV, which asymmetry potential by and by sank to a value of little below than 2.5 mV.

Contrary to this the inventive calcium-selective membrane showed in the test already at the beginning of the determination an asymmetry potential of 0 mV.

Analogous results were obtained with the two kinds of inventive sodium selective electrodes tested and the two kinds of sodium selective electrodes for comparison. In this case the electrolyte solution used at one side of the membrane was a 0.1 molar sodium chloride solution.

The corresponding tests were also performed with the inventive potassium selective membranes and the potassium selective membranes for comparison. In said tests the one side of the valinomycine containing membrane was contacted with a 0.1 molar potassium chloride solution.

EXAMPLE 6

Determination of the Concentration of Sodium Ions using Electrolyte Solutions and Samples of Serum The tests were performed with the inventive sodium selective membranes described in example 3, respectively the corresponding sodium selective membranes for comparison. The membranes contained an ion selective component, N,N,N',N'-tetracyclohexyl-1,2-phenylene-dioxi-diacetamide.

The EMF was determined with a cell of the following type:

Hg; Hg$_2$Cl$_2$, KCl (sat.) | 1M LiOAc | sample solution | | membrane | | inner filling solution, AgCl; Ag.

The inner filling solution of the electrode was a 0.1 molar solution of potassium chloride and the ion selective membranes were mounted on the body of said electrodes. The reference electrode used was the electrode described in the above stated publication of R. E. Dohner et al. in Analytical Chemistry, volume 58, 1986, page 2585 and ff.

There were used three different aqueous sample solutions which are named $A_1$, $A_2$ and $A_3$.

All said three sample solutions were aqueous solutions which contained 4.0 mM of KCl, 1.1 mM of CaCl$_2$ and 0.6 mM of MgCl$_2$ and, furthermore, different concentrations of NaCl. The aqueous solution $A_1$ contained 50 mM of sodium-chloride, the aqueous solution $A_2$ 140 mM of sodium-chloride and the aqueous solution $A_3$ 400 mM of sodium-chloride.

There were, furthermore, used as sample solutions three serum samples $S_1$, $S_2$ and $S_3$ and also said three serum samples contained different concentrations of sodium ions.

The serum sample $S_1$ contained 141 mM of Na$^+$, the serum sample $S_2$ contained 171 mM of Na$^+$ and the serum sample $S_3$ contained 211 mM of Na$^+$.

First the EMF of the sodium selective membranes for comparison and the inventive sodium selective membranes was determined, if as sample solution there was used the above mentioned aqueous solution $A_1$, respectively the aqueous solution $A_2$, respectively the aqueous solution $A_3$. The corresponding results of the sodium selective membranes for comparison are illustrated in FIG. 1 and the results of the inventive sodium selective electrodes are illustrated in FIG. 2.

Figure 1:
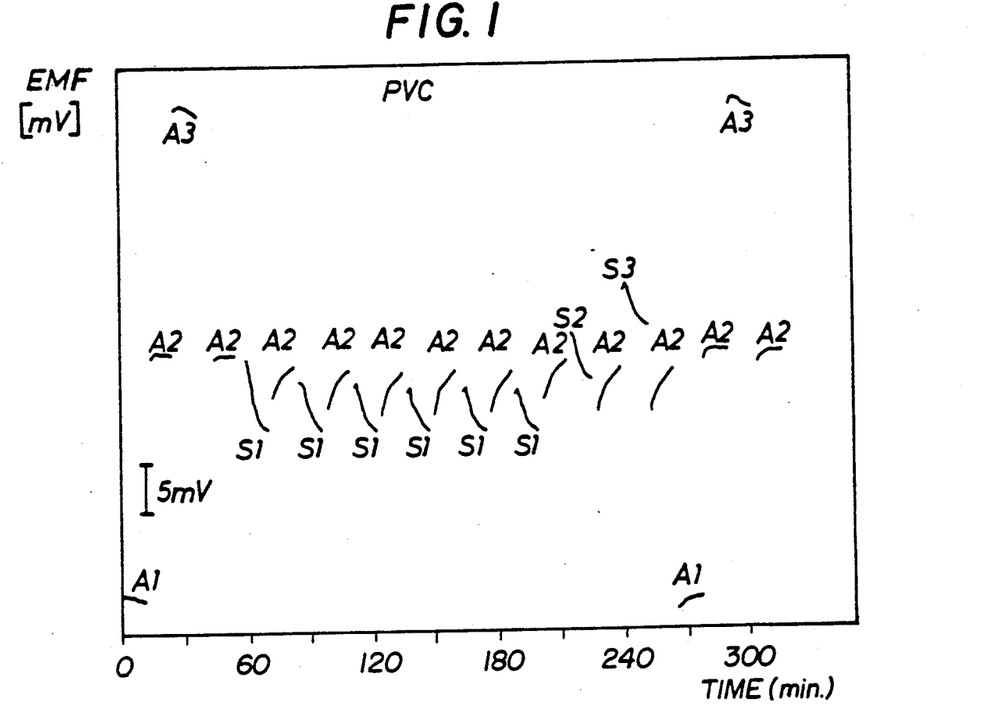
Figure 2:
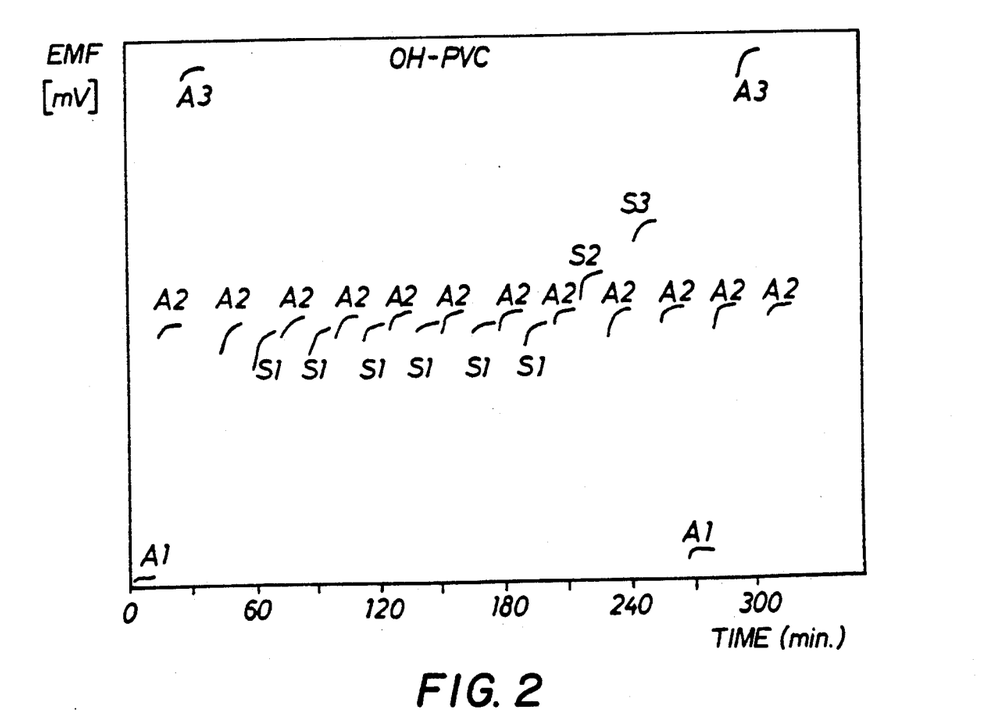

In said FIGS. 1 and 2 there is plotted on the ordinate the EMF in mV and on the abscissa there is plotted the time in minutes.

In FIG. 1 there are illustrated the results of the determinations performed with the sodium selective membranes for comparison and in FIG. 2 there are illustrated the results of the determinations performed with the inventive sodium selective electrodes. In FIG. 1 and in FIG. 2 at the left side, near to the time of 0 minutes and immediately after the time there are plotted the EMF values of the determinations performed with the aqueous sample solutions $A_1$, $A_2$ and $A_3$. Thereafter with the membranes for comparison and also with the inventive membranes once more the EMF was determined with the aqueous sample solution $A_2$. Then there follows a series of EMF values in which the determinations were performed by using alternating the serum sample $S_1$, thereafter the aqueous sample $A_2$, again the serum sample $S_1$, thereafter the aqueous sample $A_2$ and so on.

It can be clearly seen from FIG. 1 that the determined value of the EMF of the aqueous solution $A_2$ does not remain constant after the membrane for the first time had been contacted with the serum sample $S_1$. It is evident that the first and second value of $A_2$ on the FIG. 1 are about the same, while the third value $A_2$ (which follows after the first value of $S_1$) has a lower range of the EMF. Further contacts of the membrane for comparison with the serum sample $S_1$ result in that the determined value of the EMF of the aqueous sample solution $A_2$ is shifted to still lower ranges of the EMF.

FIG. 2 clearly shows that said deficiency of the membranes for comparison is not to be found with the inventive sodium selective membranes. It can be seen from FIG. 2 that the two values of the EMF of the sample solution $A_2$, which were determined before the contact of the corresponding membrane with the serum sample $S_1$, are both equal to the third value $A_2$ which was determined after the inventive sodium selective membrane had been contacted for the first time with the serum sample $S_1$. Also here a series of determinations was performed in which after the determination with the serum sample $S_1$ there follows a determination with the sample solution $A_2$ and then again a determination with the serum sample $S_1$ and a determination with the sample solution $A_2$ and so on. It can be clearly seen from said FIG. 2 that after several contacts of the inventive membrane with the serum sample $S_1$ the determined values which were measured using the sample solution $A_2$ remained constant.

It, accordingly, can be seen from FIG. 1 and FIG. 2 that the ion sensitive membranes for comparison in which the polymer component is free of any hydrophilic groups yield progressively lower values of the EMF determined after the corresponding membranes had been contacted with serum samples. Contrary to this the determined values remain constant after the inventive sodium selective membranes had been contacted several times with corresponding serum samples.

At the end of the tests illustrated in FIG. 1 and FIG. 2, the sodium selective membranes for comparison and the inventive sodium selective membranes were contacted with a further serum sample $S_2$ and then again the EMF of the aqueous solution $A_2$ was determined, thereafter the membrane for comparison and also the inventive membrane was contacted with the serum sample $S_3$ and the EMF of said serum sample was determined and thereafter again the membranes were used for the determination of the EMF of the aqueous sample $A_2$. Thereafter with the membranes for comparison and with the inventive membranes there were performed determinations of the EMF of the three aqueous solutions $A_1$, $A_2$ and $A_3$. It can be seen from FIG. 1 that the determined EMF of the aqueous samples $A_1$, $A_2$ and $A_3$ before the corresponding membranes had been contacted with the serum samples $S_1$, $S_2$ and $S_3$, clearly differ from the determined EMF of the aqueous samples $A_1$, $A_2$ and $A_3$ after the membranes for comparison had been in contact with the stated serum samples. Accordingly, the contact of the prior art membranes with protein containing materials results in a falsification of the determined EMF.

It, furthermore, can be seen from FIG. 2 that contrary to this the inventive sodium selective membranes give correct values of the determined EMF after they had been in contact with the serum samples $S_1$, $S_2$ and $S_3$. Also after the membranes had been contacted several times with serum samples, a repetition of the determination of the EMF of the aqueous sample solutions $A_1$, $A_2$ and $A_3$ yield values which are equal or nearly equal to the corresponding values which were determined at the beginning of said test series.

The results illustrated in FIGS. 1 and 2, accordingly, demonstrate clearly that the sodium selective membranes for comparison in which the polymer component was the polyvinylchloride homopolymer yielded false results of the EMF, after the membrane had been contacted for the first time with a serum sample. The false values of the EMF determined were due to a not constant standard potential $E_o$ and due to the development of an asymmetry potential.

Contrary to this, the results of FIG. 2 illustrate that corresponding inventive ion sensitive membranes in which the polymer component was a copolymer of 87.7 mol-% of vinylchloride plus 12.3 mol-% vinylalcohol yielded constant values of the determined EMF after the membranes in question had been in contact with different serum samples.

Further tests were performed with corresponding sodium selective membranes for comparison in which the polymeric component was a copolymer of vinylchloride plus vinylalcohol, in which copolymer, however, only 3 mol-% of the monomeric units were derived from vinylalcohol. The membranes for comparison, accordingly, had a too low content of hydrophilic groups. The test results showed that in the membranes for comparison the determined EMF was again too low after the corresponding membranes for comparison had been in contact with the serum samples. Accordingly, the membranes for comparison had about the same deficiencies as the membranes for comparison in which the polymeric component was a polyvinylchloride homopolymer.

The results of the determination with the membranes containing the polyvinylchloride copolymer with too low content of hydrophilic groups are not illustrated because they are very similar to the results which were achieved with the polyvinylchloride homopolymer free of any hydrophilic groups, which results are illustrated in FIG. 1.

It, accordingly, is impossible to achieve the advantages of the inventive ion selective parts if instead of the polymeric component, containing the amount of hydrophilic groups defined before, there is used a polymeric component in which clearly less than 5 mol-% of the monomeric components of the polymeric materials are substituted with the stated hydrophilic groups.

EXAMPLE 7

According to the procedure described in example 6, now the calcium selective membranes for comparison described in example 3 and the inventive calcium selective membranes described in example 3 were tested.

In the series of tests, there were as well used three aqueous solutions named $A_1$, $A_2$ and $A_3$ which aqueous solutions contained 140 mM of NaCl, 4.0 mM of KCl and 0.6 mM of $MgCl_2$ and, furthermore, different quantities of $CaCl_2$ stated thereafter.

The aqueous solution $A_1$ contained 1 mM of $CaCl_2$, the aqueous solution $A_2$ contained 3 mM of $CaCl_2$ and the aqueous solution $A_3$ contained 9 mM of $CaCl_2$.

In said series the procedure was similar to the one described in example 6, i.e. with the calcium selective membranes for comparison and with the calcium selective inventive membranes the EMF of the aqueous solutions $A_1$, $A_2$ and $A_3$ was determined. Thereafter, alternating determinations of the EMF were performed with the aqueous sample solution $A_2$ and with the serum sample solution $S_1$.

Also here the determined value of the EMF of the aqueous solution $A_2$ was lower after the membrane for comparison had been contacted for the first time with the serum sample and the value sank continuously after several contacts of the membrane for comparison with the serum sample. The results, accordingly, were similar to the results of FIG. 1 (which were obtained with the corresponding sodium selective electrodes for comparison).

Contrary to this also the inventive calcium selective electrodes yielded constant values of the determined EMF of the aqueous solutions $A_1$, $A_2$ and $A_3$ after the membranes had been in contact with the serum solution $S_1$ and with the further serum solutions $S_2$ and $S_3$.

The results of the calcium selective electrodes for comparison and the inventive calcium selective electrodes are accordingly very similar to the corresponding results achieved with the sodium selective electrodes for comparison and the inventive sodium selective electrodes respectively.

A further series of tests was performed with potassium sensitive membranes for comparison and inventive potassium selective membranes, and in the series the potassium sensitive component of the membranes was valinomycin. Also here the first contact of the membrane for comparison with the serum sample lowered the value of the determined EMF of the aqueous solution while the corresponding value remained constant if the determinations were performed with the inventive potassium selective membranes.

The potassium sensitive membranes for comparison and the inventive potassium sensitive membranes used in the test are the corresponding membranes described in example 3.

What is claimed is:

1. An ion selective member for an apparatus for determining the concentration of ions in a liquid media such that the standard potential ($E_0$) of the Nicolsky Eisenmann equation does not substantially shift and a substantial asymmetry potential is not formed, said ion selective member comprises:
   a. an ion selective component having selectivity for the ions, the concentration of which is to be determined in the liquid media; and
   b. a polymeric material that is a copolymer derived from monomeric units selected from the group of unsubstituted alkenes, unsubstituted alkynes, substituted alkenes and substituted alkynes, and combinations thereof, wherein,
      i. the substituents on the substituted alkenes and substituted alkynes are selected from the group of halide atoms, aryl groups, carboxylic ester groups, carboxylic amide groups, nitrile groups, sulfonic acid ester groups, sulfonamide groups, phosphonic acid ester groups, phosphonic acid amide groups, esterified hydroxy groups, etherified hydroxy groups, keto groups, free aldehyde groups, acetalized aldehyde groups, and combinations thereof,
      ii. said copolymer contains a backbone carbon chain selected from the group of carbon chains free of interrupting groups and carbon chains interrupted by moieties selected from the group of ethers, polyethers, esters, polyesters, urethanes, polyurethanes, amides, polyamides, carbonates, polycarbonates and combinations thereof, and
      iii. 5-25 mol % of the monomeric units of said copolymer are substituted with hydrophilic substituents selected from the group of hydroxy groups, carboxylic acid groups, sulfonic acid groups, phosphonic acid groups and combinations thereof.

2. An ion selective member according to claim 1, wherein the nonhydrophilic monomeric units of said copolymer are other than unsubstituted ethylene units.

3. An ion selective member according to claim 2, wherein said copolymer is selected from the group comprising polyvinylhalide copolymers and a polyvinylidenehalide copolymers, wherein 5-25 mol % of the monomeric units of said polymers are substituted with hydrophilic substituents selected from the group of hydroxy groups, carboxylic acid groups, sulphonic acid groups, phosphonic acid groups and combinations thereof, and said copolymer is free of any further substitutions.

4. An ion selective member according to claim 3, further comprising substituents selected from the group of ester groups, acid amide groups, nitrilo groups, carbonate groups, urethane groups and combinations thereof.

5. An ion selective member according to any of claims 3 or 4, wherein said polyvinylhalide copolymer and said polyvinylidenehalide copolymer contain a halide atom that is a chlorine atom.

6. An ion selective member according to claim 5, wherein said polymeric material is a copolymer selected from the group of:
(a) copolymers of vinylchloride and vinylalcohol;
(b) copolymers of vinylchloride, vinylalcohol, and a carboxylic acid selected from the group of unsaturated monocarboxylic acids and polycarboxylic acids; and
(c) copolymers of vinylchloride and vinylalcohol which additionally contain ester-substituted monomeric units in which the ester substituents are selected from the group of esterified hydroxy groups, esterified carboxylic acid groups and combinations thereof, and wherein 7.0-18.2 mol % of the monomeric units of said copolymer are selected from the group of moieties of vinylalcohol, moieties of unsaturated monocarboxylic acid, moieties of polycarboxylic acid, and combinations thereof.

7. An ion selective member according to claim 6, wherein the polymeric material is a copolymer selected from the group of copolymers of vinylchloride and vinylalcohol, and copolymers of vinylchloride, vinylalcohol and vinylacetate, wherein 7.0-18.2 mol % of the monomeric units of said copolymer comprise monomeric units of vinylalcohol.

8. An ion selective member according to claim 7, wherein 10.9-13.8 mol % of the monomeric units of said copolymer comprise monomeric units of vinylalcohol.

9. An ion selective member according to claim 1, further comprising a plasticizer.

10. An ion selective member according to claim 9 comprising:
0.5-5 wgt % of an ion selective component;
30-50 wgt % of polymeric material that is a copolymer; and
50-70 wgt % of a plasticizer.

11. An ion selective member according to any of claims 3 or 4, further comprising a plasticizer.

12. An ion selective member according to claim 11 comprising:
0.5-5 wgt % of an ion selective component;
30-50 wgt % of a polymer material that is a copolymer; and
50-70 wgt % of a plasticizer.

13. An ion selective member according to claim 6, further comprising a plasticizer.

14. An ion selective member according to claim 13 comprising:
0.5-5 wgt % of an ion selective component;
30-50 wgt % of a polymeric material that is a copolymer; and
50-70 wgt % of a plasticizer.

15. An ion selective member according to claim 7, further comprising a plasticizer.

16. An ion selective member according to claim 8, further comprising a plasticizer.

17. An ion selective member according to claim 15, wherein said ion selective member comprises:
0.5-5 wgt % of an ion selective component;
30-50 wgt % of a polymeric material that is a copolymer; and
50-70 wgt % of a plasticizer.

18. An ion selective member according to claim 16, wherein said ion selective member comprises:
0.5-5 wgt % of an ion selective component;
30-50 wgt % of a polymeric material that is a copolymer; and
50-70 wgt % of a plasticizer.

19. An ion selective member according to claim 1, wherein said ion selective member is suited for determining the concentration of a selected ion in a liquid media which contains, in addition to the selected ion, high molecular weight organic materials containing hydrophilic groups.

20. An ion selective member according to claim 19, wherein said liquid media is selected from the group of body fluids, whole blood, blood serum and blood plasma.

21. An ion selective member according to any of claims 25, 43 or 44, which is selected from the following group of ion selective member forms:
(a) an ion selective coating of a semi-conductor;
(b) an ion selective coating of a conductor;
(c) an ion selective membrane; and
(d) an ion selective member in a miniaturized test system for determining the concentration of several ions, wherein said miniaturized test system comprises several ion selective regions in proximity to each other, each ion selective region having selectivity for a different ion.

22. An apparatus equipped with an ion selective member for determining the concentration of ions in liquid media such that the standard potential ($E_0$) of the Nicolsky-Eisenmann equation does not substantially shift and a substantial asymmetry potential is not formed, said ion selective member comprising:
(a) an ion selective component having selectivity for the ions, the concentration of which is to be determined in the liquid media; and
(b) a polymeric material that is a copolymer derived from monomeric units selected from the group of unsubstituted alkenes, unsubstituted alkynes, substituted alkenes and substituted alkynes, and combinations thereof, wherein,
(i) the substituents on the substituted alkenes and substituted alkynes are selected from the group of halide atoms, aryl groups, carboxylic ester groups, carboxylic amide groups, nitrile groups, sulfonic acid ester groups, sulfonamide groups, phosphonic acid ester groups, phosphonic acid amide groups, esterified hydroxy groups, etherified hydroxy groups, keto groups, free aldehyde groups, acetalized aldehyde groups, and combinations thereof, (ii) said copolymer contains a backbone carbon chain selected from the group of carbon chains free of interrupting groups and carbon chains interrupted by moieties selected from the group of ethers, polyethers, esters, polyesters, urethanes, polyurethanes, amides, polyamides, carbonates, polycarbonates and combinations thereof, and (iii) 5-25 mol % of the monomeric units of said copolymer are substituted with hydrophilic substituents selected from the group of hydroxy groups, carboxylic acid groups, sulfonic acid groups, phosphonic acid groups and combinations thereof.

* * * * *